United States Patent [19]

Karpf

[11] Patent Number: 5,000,166

[45] Date of Patent: Mar. 19, 1991

[54] IMPLANT KIT FOR STABILIZING REGIONS OF A SPINE

[75] Inventor: Kurt Karpf, Holderbank, Switzerland

[73] Assignees: Sulzer Brothers Limited, Winterthur; Allo Pro AG, Baar, both of Switzerland

[21] Appl. No.: 336,838

[22] Filed: Apr. 12, 1989

[30] Foreign Application Priority Data

Apr. 27, 1988 [CH] Switzerland ................ 1577/88

[51] Int. Cl.$^5$ ............................................. A61F 5/00
[52] U.S. Cl. .......................................... 128/69; 606/61
[58] Field of Search ........................... 128/69; 606/61; 24/230.5 R, 230.5 AD; 248/316.6

[56] References Cited

U.S. PATENT DOCUMENTS

| | | | |
|---|---|---|---|
| 4,289,123 | 9/1981 | Dunn | 128/84 R |
| 4,433,676 | 2/1984 | Bobecko | 606/61 |
| 4,611,582 | 9/1986 | Duff . | |
| 4,648,388 | 3/1987 | Steffee | 128/69 |
| 4,854,304 | 8/1989 | Zielke | 128/69 |

FOREIGN PATENT DOCUMENTS

| | | |
|---|---|---|
| 0140790 | 5/1985 | European Pat. Off. . |
| 0220736 | 5/1987 | European Pat. Off. . |
| 2603983 | 8/1977 | Fed. Rep. of Germany . |
| 2834891 | 1/1980 | Fed. Rep. of Germany . |
| 2320078 | 3/1977 | France . |
| 2615095 | 11/1988 | France ................ 128/69 |
| 0646857 | 12/1984 | Switzerland . |
| WO87/01026 | 2/1987 | World Int. Prop. O. . |

OTHER PUBLICATIONS

M. Hackenbroch, et al., Orthopadisch-Chirurgischer Operationsatlas, vol. III, Thieme-Verlag Stuttgart, 1974.

*Primary Examiner*—V. Millin
*Assistant Examiner*—P. Kilbel

[57] ABSTRACT

The implant kit for stabilizing regions of a spine employs a plurality of fixing bands which are at least similar to one another and stabilizing elements which are adapted to be secured to the bands. Each fixing band is provided with bores at the opposite ends for securement to a spondyle as well as trough-like recesses in an intermediate portion for receiving the stabilizing elements and/or a correcting instrument. The components can be used for all regions of a spine.

10 Claims, 2 Drawing Sheets

IMPLANT KIT FOR STABILIZING REGIONS OF A SPINE

This invention relates to an implant kit for stabilizing regions of a spine.

As is known, a wide range of methods and appliances have been used for correcting deformations of the spine with different instruments and implants being used for the various regions of the spine (see e.g. M. Hackenbroch and A. N. Witt "Orthopadisch-chirurgischer Operationsatlas", Vol. III, Thieme-Verlag Stuttgart, 1974). This multiplicity leads to a large number of different implants and instruments which require extensive storage.

Swiss Patent 646,857 describes a spondylodesis stabilizer in which four identical tabs or links or the like are fixed by bone screws in adjacent spondyles and pins having two opposite screwthreads are screwed into each tab as stabilizers. These pins, which connect the tabs in a rigid manner, fix the two spondyles relative to one another. A rotation of the pins to either hand increases or shortens the between-tabs distance. The forces which the stabilizers exert on the spondyles, however, are transmitted basically in spots, and, thus, lead to local load peaks.

Other types of spondyar stabilizing appliances have also been described in U.S. Pat. No. 4,289,123 which employ threaded adjustment rods; in European Patent Applications 0220736 and 0140790 which employ elongated rods and screws; in U.S. Pat. No. 4,611,582, German O.S. 2834891 and International Application W087/01026 which employ clamping elements on the spondyles; and in German O.S. 2603983 and French Patent 2,320,078 which employ elongated plates and screws for stabilizing purposes.

Accordingly, it is an object of the invention to provide an implant kit for correcting regions of a spine which uses a minimum of components.

It is another object of the invention to avoid local load peaks in components used for stabilizing a spinal region.

It is another object of the invention to distribute a loading over a relatively large area in an implant for stabilizing regions of a spine.

Briefly, the invention provides an implant kit for stabilizing regions of a spine which is composed of a plurality of fixing bands and a plurality of stabilizing elements for selective securement between pairs of the fixing bands.

Each fixing band is provided with a bore at each of two opposite ends for receiving a fixing element to secure the band to a spondyle as well as a plurality of connection zones between the ends to which the stabilizing elements may be secured.

The kit comprises a reduced number of similar basic elements which can be used in all the regions of the spine and by means of which the forces produced by means of a stabilizing or correcting instrument are distributed over a very large area to the spondyles by which the basic element have been fixed. The fixing bands of the kit are at least similar to one another with at least some of the bands being identical in construction.

Irrespective of the nature, shape and size of the stabilizing elements, similar fixing bands are used in all spinal regions and are secured by bone screws or expandable plugs to spondyles forming the top and bottom boundaries of the zone to be corrected. Since the fixing position on the spondyle are interconnected by a web-like construction of the fixing bands, forces distributed over greater zones of the spondyle bodies than in the previously known constructions.

A required connection of a spinal region is made by means of a correcting instrument which is secured temporarily to each of the connection zones of previously positioned fixing bands. Thereafter, the stabilizing elements are secured to one or more of the connection zones of the fixing bands before the correcting instrument is removed. The presence of a plurality of connection zones permits a simultaneous securement of the correcting instrument and at least one stabilizing element. Of course, the connection zones occupied by the instrument may also be used after removal of the instrument for fixing another stabilizing element.

In one embodiment the connection zones of the fixing bands are in the form of trough-like recesses adapted to receive corresponding raised mating shapes of the stabilizing elements so as to provide a particularly stable connection of the stabilizing element to the fixing band. In addition, each trough-like recess is formed with a tapped bore to receive a screw for fixing of a stabizizing element to the fixing band.

In order to be able to accommodate different spondyle sizes, a number of the fixiig bands of the kit are constructed in the same manner with respect to the position of the connection zones relative to each other and to a center plane of the fixing band. However, the spacing of the bores for the fixing bands is varied in stepped manner from band to band.

In order to provice for a connection at the junction between the bottom lumbar spondyle and the sacrum, one or more fixing bands is provided with a pair of tabs which extend perpendicularly from opposite ends for securement to the sacrum.

These and other objects and advantages of the invention will become more apparent from the following detailed description taken in conjunction with the accompanying drawings wherein.

Figure 3:
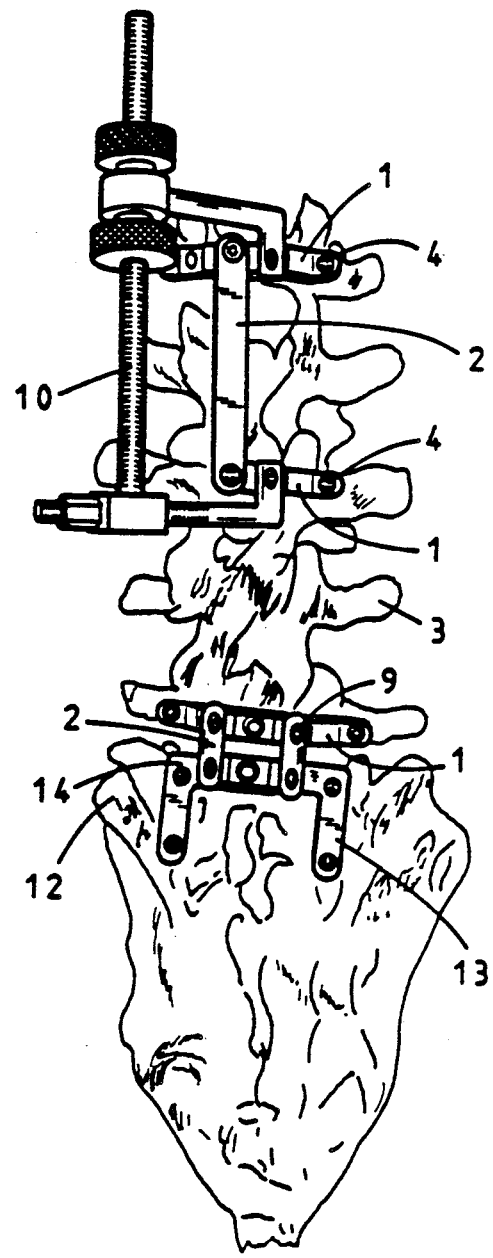
FIG. 3 illustrates a diagrammatic view of the components of an implant kit of the invention in place within a spinal column.

Referring to FIG. 3, the implant kit is provided for stabilizing regions of a spine. To this end, the kit includes a plurality of fixing bands 1 and a plurality of stabilizing elements 2, for example, which are in the form of distraction or contraction plates of different lengths which extend between spondyles 3.

Figure 1:
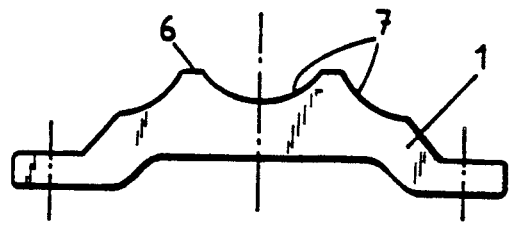
FIG. 1 illustrates a side view of a fixing band constructed in accordance with the invention'.
Figure 2:
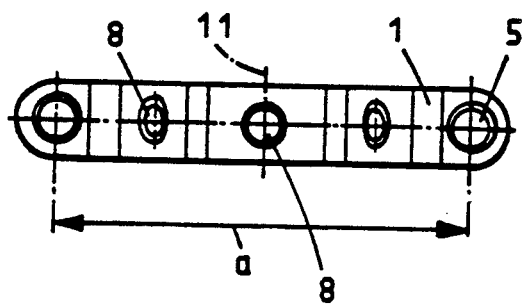
FIG. 2 illustrates a top view of the fixing band of FIG. 1.

Referring to FIGS. 1 and 2, each fixing band 1 is in the form of a web having a pair of ends and a raised central portion extending in bridging relation between the ends. Each end is provided with a bore 5 for receiving a fixing element, such as a clamping screw 4 (see FIG. 3) to secure the band 1 to a spondyle 3. Each screw 4 may, in turn be anchored within a spondyle 3 by means of an expandable plug (not shown). The raised central portion has a pair of tooth-like protuberances 6 which serve to define a plurality of trough-like recesses 7, each of which defines a connection zone. In addition, each of the three connection zones is provided with a tapped or threaded bore 8.

Referring to FIG. 3, each stabilizing element 2 is in the form of a strip-like plate having a bore at each end for alignment with a threaded bore 8 of a fixing band 1. In addition, screws 9 are provided for mounting the respective stabilizing elements 2 in the recesses 7 of the respective fixing bands 1. In order to stabilize the connection between the stabilizing elements 2 and fixing bands 1, the stabilizing elements 2 may be provided with "journals" or other suitable mating surfaces on the backside which, are adapted to the recesses 7.

Referring to FIG. 3 in order to use the components of the kit, a pair of fixing bands 1 are first secured to a pair of spondyles 3 via bone screws 4. Thereafter, a correcting instrument is secured in corresponding recesses 7 in the bands 1 to contract or distract the "overstrained spondyle 3". Once the relative positions of the spondyles 3 to one another have been corrected, one or more stabilizing elements 2 is secured to the pair of fixing bands 1 so as to maintain the corrected distance between the spondyles 3. The correcting instrument 10 may then be removed with another stabilizing element 2 being disposed across the recesses 7 previously occupied by the instrument 10.

All of the fixing bands 1 of a kit can be identical. That is, all of the fixing bands may have an identical distance a between the bores 5 at the ends of the band 1. In addition, the bores 8 in the raised central portion may be in the same position relative to one another and to a center plane 11 of symmetry. However, the bands may also be just similar, in which case, particularly, the spacing a between the bores 5 differ from one another in stepped manner to permit adaptation to different spondyle "sizes".

Figure 4:
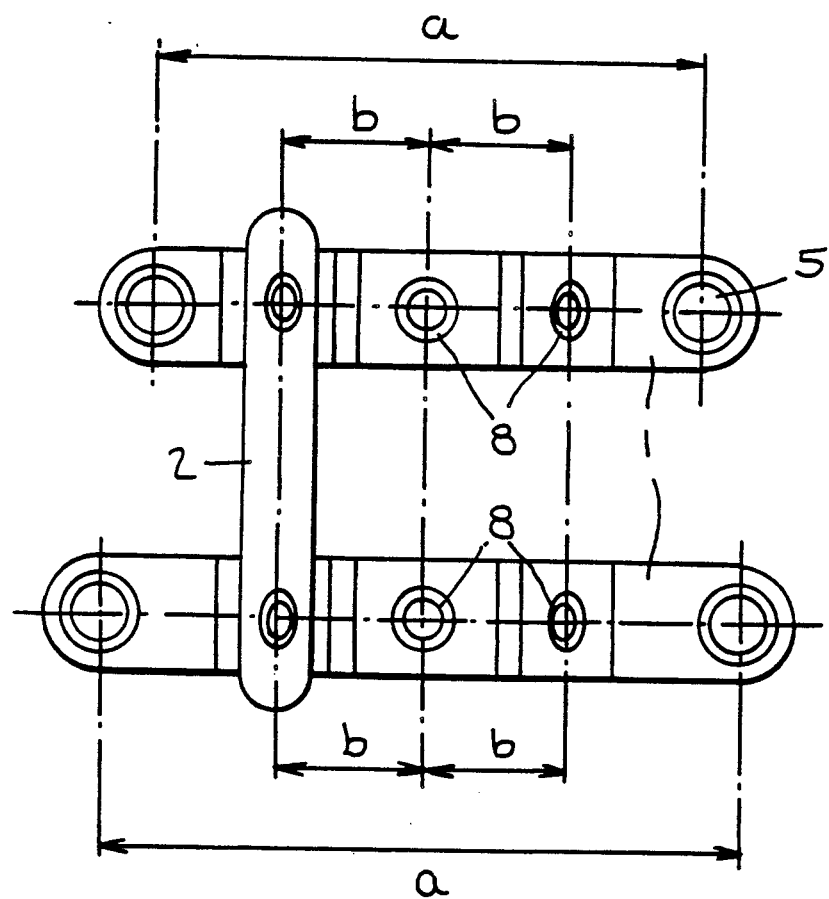
FIG. 4 illustrates a view of a pair of fixing bands interconnected by as stabilizing element in accordance with the invention.

Referring to FIG. 4, wherein like reference characters indicate like parts as above, some of the fixing bands 1 may have a spacing a between the bores 5 thereof which varies in steps from band to band while the connection zones of the bands remain in a fixed position relative to a center plane thereof. As illustrated, the bores 8 in the recess 7 remain at a fixed spacing b from the center plane.

The implant kit may also include fixing bands which are just similar to one another in the sense that all have the same shape but which differ not only with regard to the spacing a but also with respect to the position of the recesses 7 and/or bores 8.

In order to provide for a connection at the sacrum 12, at least one fixing band 14 is provided which has a pair of tabs 13 extending perpendicularly from opposite ends for securement to the sacrum 13.

With a pair of fixing bands 1 secured in place by stabilizing elements 2, the forces produced by the correcting instrument 10 can be distributed over a very large area to the spondyles 3 via the fixing bands 1.

The invention thus provides an implant kit which has a minimum of components in order to effect a connection to the spondyles of a spine in order to stabilize a particular region of the spine.

The invention further provides an implant kit with a minimum of components so that a multiplicity of special implants for discrete regions of a spine can be drastically reduced.

Further, the invention provides a connection to be made by means of a correcting instrument and to have the connection stabilized in a relatively simple manner using the components of the kit.

What is claimed is:

1. An implant kit for stabilizing regions of a spine, said kit including
    a plurality of fixing bands, each band having a transverse bore at each of two opposite ends for receiving a fixing element to secure said band to a spondyle and a plurality of connection zones between said ends; and
    a plurality of stabilizing elements for selective securement between pairs of said fixing bands, each said stabilizing element being securable to a respective connection zone of a respective fixing band.

2. A kit as set forth in claim 1 wherein each connection zones has a trough-like recess having a tapped bore therein.

3. A kit as set forth in claim 1 wherein some of said fixing bands have a spacing between said bores thereof which varies in steps from band to band and said connection zones of said latter bands are in a fixed position relative to a center plane thereof.

4. A kit as set forth in claim 1 wherein at least one fixing band has a pair of tabs extending perpendicularly from opposite ends for securement to a sacrum.

5. An implant kit for stabilizing regions of a spine, said kit comprising
    a plurality of fixing bands, each said band having a pair of ends and a raised central portion extending in bridging relation between said ends, each said end having a bore for receiving a fixing element to secure said fixing band to a spondyle, and said central portion having a plurality of trough-like recesses defining connection zones; and
    a plurality of stabilizing elements, each said element being securable between a pair of said fixing bands in a respective connection zone of each said band.

6. A kit as set forth in claim 5 wherein each recess has a threaded bore.

7. A kit as set forth in claim 5 wherein said stabilizing elements include strip-like plates of different lengths.

8. A kit as set forth in claim 7 wherein each plate has a bore at each opposite end thereof for alignment with a threaded bore of a connection zone of a respective fixing band.

9. A kit as set forth in claim 5 wherein each band has a pair of protuberances defining a centrally disposed trough-like recess therebetween.

10. A kit as set forth in claim 5 wherein at least one fixing band has a pair of tabs extending perpendicularly from opposite ends for securement to a sacrum.

* * * * *

UNITED STATES PATENT AND TRADEMARK OFFICE
CERTIFICATE OF CORRECTION

PATENT NO. : 5,000,166
DATED : March 19, 1991
INVENTOR(S) : KURT KARPF It is certified that error appears in the above-identified patent and that said Letters Patent is hereby corrected as shown below:

```
Column 1, line 27 change "spondyar" to -spondylar-
Column 1, line 51 change "cach" to -each-
Column 1, line 61 change "element" to -elements-
Column 2, lines 1 and 2 change "position" to -positions-
Column 2, line 2 change "Spondyle" to -spondyles-
Column 2, line 3 change "forces" to -forces are-
Column 2, line 24 change "stabizizing" to -stabilizing-
Column 2, line 27 change "fixiing" to -fixing-
Column 2, line 50 change "as" to -a-
Column 3, line 12 change "which," to -which-
Column 4, line 24 change "zones" to -zone-
```

Signed and Sealed this

Twenty-second Day of March, 1994

Attest:

BRUCE LEHMAN

*Attesting Officer*   *Commissioner of Patents and Trademarks*